United States Patent [19]
McEntee

[11] Patent Number: 5,885,608
[45] Date of Patent: Mar. 23, 1999

[54] LIPID SOLUBLE FORMS OF THIAMINE FOR PREVENTION AND TREATMENT OF AGE-RELATED COGNITIVE IMPAIRMENT OF THE NERVOUS SYSTEM

[76] Inventor: William J. McEntee, 313 The Esplanade South, Venice, Fla. 34285

[21] Appl. No.: 18,295

[22] Filed: Feb. 4, 1998

Related U.S. Application Data

[62] Division of Ser. No. 827,799, Apr. 11, 1997, Pat. No. 5,843,469.
[51] Int. Cl.$^6$ ................ A61F 2/02; A61F 6/06; A61F 9/02; A61K 9/48
[52] U.S. Cl. .......... 424/423; 424/427; 424/430; 424/433; 424/434; 424/436; 424/439; 424/451; 424/464
[58] Field of Search ................. 424/423, 427, 424/430, 433, 434, 436, 439, 451, 464

[56] References Cited

PUBLICATIONS

Mimori et al, "Thiamine Therapy in Alzheimer's Disease", Metabolic Brain Disease, vol. 11, No. 1 pp. 89–94, 1996.
Lonsdale et al, "Brainstem Dysfunction in Infants Responsive to Thiamine Disulfide Preliminary Studies in Four Patients", Clinical Electroencephalography, vol. 13, No. 2, pp. 82–88, 1982.

*Primary Examiner*—Carlos Azpuru
*Attorney, Agent, or Firm*—Pendorf & Cutliff

[57] ABSTRACT

A method for preventing, ameliorating, and/or treating memory and other cognitive disorders associated with aging, such as Age-Associated Memory Impairment (also known as Age-Related Cognitive Decline), and other age-related impairments of, and/or changes in, cognitive function. The method comprises administering to a subject a therapeutically effective amount of a lipid-soluble thiamine or a prodrug thereof in an amount averaging from about 0.02 to about 0.5 grams per day per 70 kg body weight over a period of three months or longer.

17 Claims, No Drawings

LIPID SOLUBLE FORMS OF THIAMINE FOR PREVENTION AND TREATMENT OF AGE-RELATED COGNITIVE IMPAIRMENT OF THE NERVOUS SYSTEM

This is a divisional of application Ser. No. 08/827,799, now U.S. Pat. No. 5,843,469 filed Apr. 11, 1997, allowed Dec. 23, 1997.

BACKGROUND OF THE INVENTION

1. Field of the Invention

The present invention is in the field of clinical neurology and relates to a method for preventing and/or treating memory and other cognitive impairments associated with aging, such as Age-Associated Memory Impairment (also known as Age-Related Cognitive Decline) and other age-related changes in cognitive function.

2. Description of the Related Art

There are many memory-related conditions for which therapeutic treatments have been under investigation, such as methods to enhance memory or to treat memory dysfunction. Certain types of memory dysfunction are believed to be linked to the aging process, as well as to neurodegenerative diseases such as Alzheimer's disease. Memory impairment can also follow head trauma or multi-infarct dementia. Many compounds and treatments have been investigated which can enhance cognitive processes and improve memory and retention abilities.

For example, the compound piracetam has been prescribed for treatment to enhance memory (Giurgea et al, Arch. Int. Pharmacodyn. Ther. 166, 238 (1967). U.S. Pat. No. 4,639,468 to Roncucci et al describe the use of the compound milacemide for treatment of memory impairment. Further investigation of milacemide has documented the memory-enhancing capabilities of milacemide in human subjects [B. Saletu et al. Arch. Gerontol. Geriatr. 5, 165–181 (1986)]. Bodor (U.S. Pat. No. 5,296,483) teaches a new approach for delivering drugs to the brain using the redox system. Specifically, the primary, secondary, or tertiary functions of centrally acting amines are replaced with a dihydropyridine/pyridinium salt redox system, and the resulting quaternary compounds provide site-specific and sustained delivery to the brain. Upon delivery to the brain, the compound is oxidized to a form which cannot readily pass the blood-brain barrier and hence is "locked" in the brain.

Riekkinen et al. (U.S. Pat. No. 5,434,177) teaches the use of $\alpha$-2-receptor antagonist imidazole derivatives for the treatment of age related cognitive disorders. Cordi et al. (U.S. Pat. Nos. 5,260,324 and 5,208,260) teach a composition containing D-cycloserine and D-alanine, and vinyl glycine derivatives, for memory enhancement or treatment of cognitive disorders, respectively.

Thiamine (vitamin B-1) is an essential nutrient and an indispensable component in the oxidation of glucose, which is the main source of cellular energy in the central nervous system (CNS). With respect to its role in cellular energy production, thiamine, in its biologically active diphosphate form, acts as a coenzyme in two mitochondrial enzyme complexes—the pyruvate dehydrogenase (PDH) and the $\alpha$-keto glutarate dehydrogenase ($\alpha$-KGDH) complexes. PHD and $\alpha$-KGDH must be sufficiently active to provide glucose oxidation rates necessary for cellular energy requirements. If thiamine availability is inadequate to attain this required enzyme activity level, then the energy-yielding metabolism derived from the oxidation of glucose will be reduced and cell integrity may be jeopardized. This is particularly true in the CNS where cells are more dependent on oxidative glucose metabolism for energy than are cells in the rest of the body.

In addition to its crucial role in cellular energy production, thiamine is: 1) an essential cofactor for activity of transketolase, an enzyme involved in biosynthetic reactions; 2) required for normal conduction of electrical impulses along nerve fibers (Cooper J. R., Pincus J. H.; The role of thiamine in nervous tissue; Neurochem. Res., 4:223–239, 1979); and 3) implicated in the synthesis and neural release of acetylcholine (Eder L., Dunant Y.; Thiamine and cholinergic transmission in the electric organ of torpedo; J. Neurochem, 35:1278–1296, 1980), a neurochemical that plays an important role in learning and memory.

Intake of thiamine in humans is accomplished by consumption of thiamine-containing foods and of commercial vitamin preparations. The recommended dietary allowance (RDA) for thiamine in the United States is roughly 0.5 mg per 1000 consumed calories.

Thiamine in its water soluble form is absorbed by the small intestine via two processes, depending upon its concentration in the intestinal lumen (Rindi G., Ventura U.; Thiamine intestinal transport; Physiol. Rev., 52:821–827, 1972; Hoyunpa A. M., Strickland R., Sheehan J. J., Yarborough G., Nichols S.; Dual system of intestinal transport of thiamine in humans; J Lab Clin Med., 99.701–708, 1982). At low concentrations (<2 micromolar) a saturable, energy-dependent active transport mechanism operates against a concentration gradient. At high concentrations (>2 micromolar) the vitamin is absorbed by passive diffusion, down a concentration gradient. In humans, there is little increase in urinary thiamine excretion at oral dosages in excess of 0.5 mg (Morrison A. B., Campbell J. A.; Factors influencing the excretion of oral test doses of thiamine and riboflavin by human subjects; J. Nutr., 72.435–444, 1960), suggesting that passive diffusion of this water soluble vitamin across the intestinal wall is not significant. However, more recent evidence suggests that high oral doses of water-soluble thiamine does produce a parallel increase in its absorption (Meador K., Loring D., Nichols M., Zamrini E., et al.; Preliminary findings of high dose thiamine in dementia of Alzheimer's type; J. Geriatr. psychiatry Neurol., 6:222–229, 1993).

Transport of water soluble thiamine across the blood brain barrier also involves two processes (Greenwood J., Love E. R., Pratt O. E.; Kinetics of thiamine transport across the blood-brain barrier in the rat; J. Physiol., 327:95–103, 1982; Reggiani C., Patrini C., Rindi G.; Transport of thiamine and thiamine monophosphate from plasma to different brain regions of the rat; Brain Res., 293:319–327, 1984): a saturable active carrier-mediated mechanism and a non-saturable mechanism which may also involve a carrier molecule (Greenwood J., Pratt O. E.; Comparison of the effects of some thiamine analogues upon thiamine transport across the blood-brain barrier of the rat; J. Physiol, 369.79–91, 1985). Entry of thiamine into brain cells is governed by an active transport system which is distinct from those that control its passage across the blood-brain barrier (Sharma S. K., Quastel J. H.; Transport and metabolism of thiamin in rat brain cortex in vitro; Biochem. J., 94. 790–800, 1965; Spector R. O.; Thiamine transport in the central nervous system; Am J. Physiol, 230:1101–1107, 1976).

The relationship between thiamine and aging is not fully understood. In free-living persons, both calorie and thiamine intake diminish with advancing age, but the USRDA intake ratio of 0.5 mg thiamine/1000 calories is maintained or exceeded in all age groups studied by Iber and coworkers (Iber F. L., Blass J. P., Brin M., Leevy C. M.; Thiamin in the elderly, relation to alcoholism and neurological degenerative disease; Am. J. Clin. Nutr., 6:1067–1082, 1982). However, even though existing data shows that thiamine intake is adequate among the aged, there is also evidence to suggest that aging is associated with changes in thiamine utilization and metabolism. Biochemical measures of thiamine function done on free-living elderly people in England revealed abnormalities suggesting severe thiamine deficiency in 15% and marginal deficiency in 53% of 118 persons studied (Griffiths L. L., Brocklehurst J. C., Scott D. L., Marks J., Blackley J.; Thiamine and ascorbic acid levels in the elderly; Gerontol. Clin., 9:1–10, 1967). Another study showed that 45% of 75 persons living in an old age home in Finland showed biochemical evidence of marginal thiamine deficiency (Roine P., Koivula L. I., Pekkarinen M. O.; Plasma vitamin C level and erythrocyte transketolase activity compared with vitamin intakes among old people in Finland; Nutrition, 4:116–120, 1972). Other studies have shown reduced excretion of thiamine in elderly humans, suggesting that its levels in tissues are lowered with age (Rafsky H. A., Newman B.; Vitamin B-1 excretion in acid; Gastroenterology, 1. 1943; Rafsky M. A., Newman B., Jolliffe N.; Relationship of gastric acidity to thiamine excretion in aged; J. Lab. Clin. Med., 32:118–123, 1947).

Animal experiments further indicate changes in thiamine needs, as well as in thiamine utilization and metabolism, with aging. These animal experiments have demonstrated that: 1) old rats require more thiamine per gram of consumed food than young rats (Mills C. A., Cottingham E., Taylor E.; Effect of advancing age on dietary thiamine requirements; Arch. Biochem., 9:221–227, 1946); 2) transport of thiamine across the intestine is significantly lower in old rats compared to younger rats (Lazarov J.; Changes in the resporption and the phosphorylation of thiamine in rats in relation to age; J. Exp. Gerontol, 12:75–79, 1977); and 3) thiamine deficiency produces a larger decrease in the activity of $\alpha$-KGDH (used in glucose oxidation) in the brains of old mice than in young mice (Freeman G. B., Nielsen P. E., Gibson G. E.; Effect of age on behavioral and enzymatic changes during thiamine deficiency; Neurobiol. Aging, 8.429–434, 1987). These data suggest that 1) thiamine intake requirements increase with aging; 2) the transport of thiamine from the intestine to the bloodstream is decreased with advancing age; 3) with aging, thiamine-dependent enzymes in the brain have an increased sensitivity to the effects of thiamine deficiency (i.e., enzyme activity is reduced by a lesser degree of thiamine deficiency in the aged than in the young).

From all of the above, it may be inferred that defective thiamine transport across the intestine may be a contributing factor in the age-related increase in thiamine requirements in relation to the amount of food consumed, while defective transport of thiamine from the blood to the brain may be an explanation for the age-related increase in thiamine deficiency sensitivity of thiamine-dependent enzymes in the brain. Accordingly, defective active transport of thiamine, whether across the intestine, the blood-brain barrier (BBB) or into brain cells, which results from the aging process, may be an important factor in the decline of memory function commonly associated with aging (Larrabee G. J., McEntee W. J., Crook T. H.; Age-Associated Memory Impairment; In cognitive Disorders: Pathophysiology and Treatment, E. R. Gamzu, W. H. Moos, L. J. Thal. (Eds) Marcel Dekker Inc, 1992; Larrabee and Crook 1994).

A connection between this age-related loss of memory abilities and abnormal thiamine function is suggested by the qualitative similarities in neuropsychological impairments demonstrated in healthy elderly persons and in younger patients with Korsakoff's disease, a learning and memory disorder linked to thiamine deficiency. Both groups perform poorly on tasks that require divided attention and both exhibit short-term memory deficits that may be due to deficient information processing (Craik; The nature of the age decrement in performance on dichotic listening tasks; Q. J. Exp. Psychol. 227–240; 1965; Glosser G., Butters N., Samuels I.; Failure of information processing in patients with Korsakoff's syndrome; Neuropsychology, 14:327–334, 1976; Butters N., Cermak L.; Alcoholic Korsakoff's syndrome: An information-processing approach to amnesia; Academic Press, New York, 1980). Furthermore, Korsakoff patients show specific deficits in performance on standardized psychometric tests that are particularly sensitive to the effects of aging. These tests include the Digit-Symbol subtest of the Wecshler Adult Intelligence Scale (Wechsler D.; Wechsler Adult Intelligence Scale; The Psychological Corporation, New York, 1955) and the Logical Memory, Visual Reproduction, and Associative Learning subtests of the Wechsler Memory Scale (Hulicka, I. M.; Age differences in Wechsler Memory Scale scores; J. Genetic Phsycol. 109:135–145; 1966).

Impaired active transport of thiamine may also play a role in the pathogenesis of age-related neurodegenerative disorders. For instance, Alzheimer's disease (AD) increases in frequency with advancing age, and a number of studies have shown that the activity of all thiamine-dependent enzymes is decreased in the brains of patients with AD at death (Perry E. K., Perry R. H., Tomlinson B. E., Blessed G., Gibson P. H.; coenzyme-A acetylating enzymes in Alzheimer disease: possible cholinergic compartment of pyruvate dehydrogenase; Neurosci. Lett., 18:105–110, 1980; Gibson G. E., Sheu R. F., Blass J. P., et al.; Reduced activities of thiamine-dependent enzymes in the brains and peripheral tissues of patients with Alzheimer's disease; Arch Neurol., 45:836–840, 1988; Butterworth R. F., Besnard A.-M.; Thiamine-dependent enzyme changes in temporal cortex of patients with Alzheimer's disease; Metab. Brain Dis., 5:179–184,1990). More recently, significant decreases in the activity of $\alpha$-KGDH in histologically normal skin fibroblasts of patients with familial AD have been reported (Sheu K.-F. R., Cooper A. J. L., Koike K., Koike M., et al.; Ann. Neurol., 35:312–318, 1994).

If age-related impairments of central nervous system function result from age-related changes in the active transport of thiamine, then attempts to correct these changes would be important in the overall effort to improve the quality of life of the elderly. Over the years, a number of studies and strategies have been designed to investigate the age-related changes in thiamine utilization and metabolism. Some studies have attempted to compensate for the age-related changes in water-soluble thiamine utilization and metabolism associated with people suffering from AD. None of these investigations have provided successful results over periods of a year or more. In a short-term clinical trial, AD patients treated daily with 3 grams of oral thiamine HCl over a period of three months showed a small, but statistically significant, improvement in performance on a single test of cognition compared to their performance during treatment with a placebo (Blass J. P., Gleason P., Brush D., et al.; Thiamine and Alzheimer's disease; Arch Neurol., 45:833–835, 1988). When this same treatment was given for more than one year, however, the small cognitive improvement seen in the 3 month trial failed to persist (Nolan K. A., Black R. S., Sheu K. F. R., et al.; A trial of thiamine in Alzheimer's disease; Arch Neurol., 48:81–83, 1991). More recently, Meador et al. (Meador K., Loring D., Nichols M., Zamrini E., et al.; Preliminary findings of high dose thiamine in dementia of Alzheimer's type; J. Geriatr. psychiatry Neurol., 6:222–229, 1993) treated a group of AD patients with higher doses of oral thiamine HCl. After taking 4–8 grams per day AD patients demonstrated a trend of improved performance on cognitive measures when compared with patient performance at baseline. However, this study did not show such improvement when comparisons were made with task performances following treatment with placebo.

Several lines of evidence suggest that changes in nervous system function which occur as an effect of aging may be related to abnormalities in the utilization and/or metabolism of thiamine. In this regard, most of the abnormalities are probably in the transport of thiamine from intestine to blood and from blood to brain.

No researcher has investigated a long term method for preventing or treating and ameliorating the memory and cognitive disorders and other nervous system impairments associated with aging, including Age-Associated Memory Impairment (also known as Age-Related Cognitive Decline) and other age-related cognitive impairments.

SUMMARY OF THE INVENTION

The present invention is concerned with the provision of a method for preventing and/or treating those impairments of the central nervous system which are associated with aging. The present invention is realized by the long-term administration of allithiamines and/or other lipid-soluble forms of thiamine in dosages and regimens safe for long term human consumption.

The current invention also relates to a method for improvement of cognitive function, or treatment of cognitive dysfunction, in geriatric patients or humans prone to thiamine deficiency by administering to a subject over an extended period of time a therapeutically effective amount of a lipid-soluble thiamine or a prodrug thereof.

More particularly, the present invention relates to the use of pharmaceutical compositions containing allithiamines or lipid-soluble thiamine forms to treat Age-Associated Memory Impairment (also known as Age-Related Cognitive Decline) and other age-related cognitive impairments.

The present invention also provides a method for maintaining or improving memory, as well as treating age-associated impairment of cognition and memory by the administration of lipid-soluble thiamine in such a regimen as to provide a sustained average daily dose of from 20 to 500 mg, preferably 20 to 100 mg, most preferably 30 to 50 mg, of lipid soluble thiamine, preferably thiamine propyl disulfide (TDP) or thiamine tetrahydrofurfuryl disulfide (TTFD), over a period ranging from 3 months to life, preferably a period in excess of one year, most preferably a period in excess of five years. In no single day should the dosage of thiamine exceed 500 mg, and the patient should not experience a period without lipid soluble thiamine supplementation longer than two months, preferably not longer than one month, most preferably not more than two weeks.

Further, the present invention provides a method of improving cognitive and memory function or treatment of a cognitive or memory dysfunction and other age-associated nervous system impairments using pharmaceutical compositions containing lipid-soluble thiamine in addition to other dietary supplements, flavorings, or in admixture with an inert, non-toxic pharmaceutical carrier.

These and other objects of the present invention will become apparent after reference to the detailed description of the invention below.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other treatment methodologies for carrying out the same purposes of the present invention. It should also be realized by those skilled in the art that such equivalent structures do not depart from the spirit and scope of the invention as set forth in the appended claims.

DETAILED DESCRIPTION OF THE INVENTION

In the following, a method will be described for preventing or treating nervous system impairments associated with aging in which a person suffering from, or liable to suffer from, a nervous system impairment, age-associated memory impairment (also known as age-related cognitive decline), and other age-related cognitive impairments, is administered a therapeutically effective amount of a formulation containing a lipid-soluble form of thiamine as the active compound. The lipid-soluble thiamine is preferably thiamine propyl disulfide (prosultiamine), thiamine tetrahydrofurfuryl disulfide (fursultiamine), thiamine allyl disulfide, thiamine (7-methoxycarbonyl-3-acetylthioheptyl)disulfide, thiamine 2-hydroxyethyl disulfide, or O-benzoylthiamine disulfide. Most preferably, the lipid-soluble thiamine is thiamine propyl disulfide, thiamine tetrahydrofurfuryl disulfide, or O-benzoylthiamine disulfide.

While not wishing to be bound to any particular theory or mode of operation, the lipid-soluble thiamine is: 1) an essential cofactor for activity of PHD, $\alpha$-KGDH and transketolase, enzymes involved in cellular energy production and biosynthetic reactions, which thereby helps prevent the cell loss typical with age-related cognitive impairments; 2) required for normal conduction of electrical impulses along nerve fibers (Cooper J. R., Pincus J. H.; The role of thiamine in nervous tissue; Neurochem. Res., 4:223–239, 1979); and 3) implicated in the synthesis and neural release of acetylcholine (Eder L., Dunant Y.; Thiamine and cholinergic transmission in the electric organ of torpedo; J. Neurochem, 35:1278–1296, 1980), a neurochemical that plays an important role in learning and memory.

Experiments have demonstrated that: 1) old rats require more thiamine per gram of consumed food than young rats; 2) transport of thiamine across the intestine is significantly lower in old rats compared to younger rats; and 3) thiamine deficiency produces a larger decrease in the activity of $\alpha$-KGDH (required for glucose oxidation) in the brains of old mice than in young mice. These data suggest that thiamine intake requirements increase with aging; the transport of thiamine from the intestine to the bloodstream is decreased in the aged; and with aging, thiamine-dependent enzymes in the brain have an increased sensitivity to the effects of thiamine deficiency (i.e., enzyme activity is reduced by a lesser degree of thiamine deficiency in the aged than in the young).

From this, it may be inferred that defective thiamine transport across the intestine may be a factor in the age-related increase in thiamine requirements in relation to the amount of food consumed, while defective transport of thiamine from the blood to the brain may explain the age-related increase in thiamine deficiency sensitivity of thiamine-dependent enzymes in the brain. Defective active transport of thiamine, whether across the intestine, the blood-brain barrier (BBB), or into brain cells, which results from the aging process may thus be an important factor in the decline of memory function commonly associated with aging. Empirical evidence considered in light of this explanation seems to support this theory.

In 1951, Japanese scientists discovered that treating thiamine with garlic extract or the extract of other allium plants yielded very biologically active thiamine forms which were less water-soluble and more lipid-soluble than the existing commercial forms. Moreover, these lipid-soluble thiamine compounds have been shown to: 1) be more readily absorbed from the intestine; 2) produce higher levels of thiamine in the blood, cerebrospinal fluid (CSF), and urine; and 3) induce less thiamine fecal loss than the water soluble thiamine hydrochloride (Takenouchi K., Aso K.; Absorption and excretion of thiamine propyl disulfide; J. Vitamin (Kyoto), 10:142–153, 1964; Nose Y., Iwashima A.; Intestinal absorption of thiamine propyl disulfide; J. Vitamin (Kyoto), 11:165–170, 1965; Thomson A. D., Frank O., Baker H., Leevy C. M.; Thiamine Propyl Disulfide: Absorption and utilization; Ann. Int. Med., 74:529–534, 1971).

A variety of these lipid-soluble (or lipophilic) thiamine compounds, known as thiamine alkyl disulfides or allithiamines, have been synthesized and are commercially available in Japan, parts of Europe, and some other countries around the world, but are not approved for human use in the United States. The lipid-soluble thiamines most commonly used in humans, where available, are: thiamine tetrahydrofurfuryl disulfide (TTFD), thiamine propyl disulfide (TPD), and O-benzoylthiamine disulfide.

The lipophilic character of lipid-soluble thiamines allows these compounds to passively diffuse through the membranes of many cells throughout the body. This passive diffusion process bypasses the energy-dependent mechanisms required to actively transport water-soluble thiamines across cell membranes. Hence, the use of lipophilic forms of thiamine should permit a greater amount of this essential nutrient to be transported from the intestine to blood, from blood to brain, and into brain cells when the normal thiamine active transport processes are deficient, as the present inventor speculates to be the case with aging.

Lipid-soluble thiamines have been used in humans on an experimental basis to investigate the short-term treatment of disorders of thiamine deficiency and thiamine metabolism, but no study has investigated long term effects of lipid soluble thiamine on patients experiencing, or liable to experience, age-related cognitive disorders. One short term study compared the effects of TPD with water-soluble thiamine hydrochloride (HCl) when given orally to thiamine-deficient alcoholics (Thompson et al. 1971). The researchers found that TPD was effective in correcting laboratory and clinical evidence of thiamine deficiency that were refractory to thiamine HCl. A 50 mg oral dose of TPD produced blood and CSF thiamine levels that were many times greater than those resulting from a 50 mg oral dose of thiamine HCl. Six of these authors' subjects displayed ocular palsies consistent with a diagnosis of Wernicke's encephalopathy, a brain disorder associated with alcoholism and caused by thiamine deficiency. In all six, the eye movement abnormalities cleared or markedly improved within six hours following 50 mg of oral TPD, while no improvement followed the same thiamine HCl dosage in three of the six subjects. No adverse effects of TPD were observed over 8 weeks of daily, 50 mg, oral treatments. The results appear to demonstrate the superiority of TPD over thiamine HCl with respect to passage of thiamine across the intestine, across the red blood cell membrane, and into the CNS in the presence of thiamine deficiency.

Pincus et al. (Pincus J. H., Cooper J. R., Murphy J. V., et al.; Thiamine derivatives in subacute necrotizing encephalomyelopathy; Pediatrics, 716–721, 1971) tried thiamine tetrahydrofurfuryl disulfide (TTFD) as a treatment of children with Leigh's disease, an inherited disorder of thiamine metabolism. These investigators demonstrated marginal improvement in cognitive function in some of their TTFD-treated patients. However, the TTFD treatments failed to produce clinically relevant improvements in cognitive function in children suffering with Leigh's disease.

Leigh et al. (Leigh D., McBurney A., McIlwain H.; Erythrocyte transketolase activity in the Wernicke-Korsakoff syndrome; Brit. J. psychiat., 139:153–156, 1981) studied TTFD as a treatment for patients with Korsakoff's disease. In that study, a daily dose (0.3 grams) of TTFD was given orally to a large group of Korsakoff patients over a period of six weeks to two years. This dose of TTFD increased the activity of transketolase in the patients' red blood cells. Conversely, a 1.0 gram daily dose of thiamine HCl had no such transketolase effect. Thus, TTFD, presumably by its ability to passively diffuse into red blood cells, produced an increase in the activity of a thiamine-dependent enzyme that could not be produced by a much larger dose of the water-soluble thiamine HCl. This suggests that active transport of thiamine is deficient in patients with Korsakoff's disease. The study does show that large doses of lipid soluble thiamine administered over periods of up to two years are safe. Nevertheless, the TTFD dose failed to produce an improvement in patients' cognitive abilities.

Mimori et al, in "Thiamine Therapy in Alzheimer's Disease", Metabolic Brain Disease, Vol. 11, No. 1, 1996, experimentally administered to patients with AD an oral dose of 100 mg/day of TTFD in a 12 week open trial, and found mild beneficial effect. However, the discussion indicated that three reports on the effect of thiamine in patients with AD have been published to date, and that the findings remain controversial. The paper concluded that the mechanism of the observed effects of thiamine or it's derivatives in patients with AD is uncertain.

The Leigh et al. (Leigh D., McBurney A., McIlwain H.; Erythrocyte transketolase activity in the Wernicke-Korsakoff syndrome; Brit. J. psychiat., 139:153–156, 1981) studies, taken together with the qualitative similarities in neuropsychological test impairments shown in Korsakoff patients and elderly persons, as discussed above, lead the present inventor to formulate a hypothesis of an age-related deficiency in the active transport of thiamine between body compartments. Moreover, the investigations by Leigh et al. (Leigh D., McBurney A., McIlwain H.; Erythrocyte transketolase activity in the Wernicke-Korsakoff syndrome; Brit. J. psychiat., 139:153–156, 1981) produced no adverse effects of TTFD treatment in their patients, indicating an ample margin of safety for the therapeutic use of TTFD in humans.

The present inventor concluded that the failure of TTFD treatment to significantly improve cognitive function in patients with Leigh's or Korsakoff's disease is probably attributable to irreversible critical brain cell loss that is characteristic of both illnesses. The inventor noted that treatment of elderly AD patients with water-soluble thiamines failed to show any positive long-term effects on memory or cognition when compared to placebo. The present inventor concluded that this is most likely due to failure of thiamine active-transport systems. In the United States and in many other parts of the world, thiamine is ingested only in water soluble forms which require intact active transport mechanisms for its proper utilization and metabolism. The use of lipid-soluble forms of thiamine, which can passively diffuse into cells, in the absence of energy-dependent active transport capability, may be an effective method to compensate for thiamine active-transport dysfunction.

Lipid-soluble thiamines have been used in humans on an experimental basis for the treatment of thiamine-deficiency disorders. The results clearly demonstrate the superiority of TPD or TTFD over thiamine HCl with respect to passage of thiamine across the intestine, across the red blood cell membrane, and into the CNS in the presence of thiamine deficiency.

The lipophilic character of lipid-soluble thiamines allows these compounds to passively diffuse through the membranes of many cells throughout the body. This passive diffusion process bypasses the energy-dependent mechanisms required to actively transport water-soluble thiamines across cell membranes. Hence, the use of lipophilic forms of thiamine should permit a greater amount of this essential nutrient to be transported from the intestine to blood, from blood to brain and into brain cells when the normal thiamine active transport processes are deficient, as appears to be the case with aging.

The use of lipid-soluble thiamines as herein described is believed to be of most therapeutic benefit as a prophylactic when given prior to or early in the onset of nervous system impairments, and more specifically when given prior to the onset of age-related nervous system diseases such as AD, as it may prevent brain cell loss which is characteristic of AD.

The lipid soluble thiamine active compound is usually administered in a pharmaceutically-acceptable formulation. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by oral administration, or by parenteral administration such as intravenous, intramuscular, subcutaneous, or other conventional routes of medication administration.

Formulations for oral administration may be in the form of capsules containing the active compound dispersed in a binder such as gelatin or hydroxypropylmethyl cellulose, together with one or more of a palliative, lubricant, preservative, surface-active or dispersing agent. Such capsules or tablets may contain a control-release formulation as may be provided in a disposition of active compound in hydroxypropylmethyl cellulose.

Formulations for oral administration may also be in the form of a food or beverage. Broadly, the food and beverage may contain various dietetically acceptable vehicles and/or additives in addition to the essential lipid-soluble thiamine. Any dietetically acceptable vehicles may be used as long as they have no adverse influence on the structure or ability of the lipid-soluble thiamine to treat impairments of the nervous system associated with aging, age-associated memory impairment (also known as age-related cognitive decline), and other age-related cognitive impairments. Examples of such vehicles may include various carriers, extenders, diluting agents, bulking agents, dispersing agents, solvents (oil, etc.), buffering gents, gelling agents, suspending agents, etc.

In a formulation for oral administration in the form of a food or beverage, any dietetically acceptable additives may be used as long as they have no adverse influence on the structure or ability of the lipid-soluble thiamine to treat impairments of the nervous system associated with aging, age-associated memory impairment (also known as age-related cognitive decline), and other age-related cognitive impairments. Examples of such additives include various vitamins (e.g. vitamin A, vitamin B2, vitamin B6 panthotenic acid, nicotinic acid, vitamin C, vitamin E, etc), sweetening agents, organic acids (e.g. citric acid, malic acid, fumaric acid, malonic acid, succinic acid, tartaric acid, lactic acid, etc.), coloring agents, flavoring agents (e.g. vanillin, linalool, natural perfumes, etc), ant-wetting agents, fibers, minerals, nutrients, antioxidants, preservatives, aromas, humectants, natural plant extracts (e.g. tea extracts, coffee extracts, cocoa extracts, fruit extracts such as orange, grape, apple, peach, pineapple, pear, plum, cherry, papaya, tomato, melon, strawberry, and raspberry, etc), etc.

For dietary purposes, the food or beverage is preferably substantially free from a caloric sweetening agent such as sucrose, fructose, glucose, and the like. More preferably, the food or beverage is sweetened with a non-sugar sweetening agent. Such non-sugar agents include aspartame, stevia, and saccharin.

The composition containing the lipid-soluble thiamine is administered in a therapeutically effective amount, that is, an amount sufficient to diminish or stop a patient's nervous system impairments associated with aging, such as age-associated memory impairment (also known as Age-Related Cognitive Decline), or other age-related cognitive impairments. Usually, the single amount administered is an amount from 0.02–0.5 grams, preferably 0.05–0.30 grams, per day for a 70 kg adult human. A suitable dose can be administered in multiple sub-doses per day. These subdoses may be administered in unit dosage forms. The composition is administered by any technique capable of introducing the compound into the bloodstream of a human patient, including oral administration, and by intravenous, intramuscular, and subcutaneous injections. Typically, a dose or subdose may contain from about 1 mg to about 0.5 g of active compound per unit dosage form. Most preferred is a dosage form containing about 3 mg to 300 mg of active compound per unit dose.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method for treating Age-Associated Memory Impairment, said method comprising administering to a subject a therapeutically effective amount of a lipid-soluble thiamine or a prodrug thereof, said lipid soluble thiamine being administered in an amount averaging from about 0.02 to about 0.5 grams per day per 70 Kg body weight over a period of at least three months.

2. A method for treating Age-Associated Memory Impairment, said method comprising administering to a subject a therapeutically effective amount of a lipid-soluble thiamine or a prodrug thereof, said lipid soluble thiamine being administered in an amount averaging from about 0.02 to about 0.5 grams per day per 70 Kg body weight over a period of at least three months, wherein said lipid-soluble thiamine is thiamine propyl disulfide.

3. The method of claim 1, wherein said administration is parenteral, and the parenteral administration is by intravenous, intramuscular, or subcutaneous route.

4. The method of claim 3, wherein the amount of lipid-soluble thiamine is administered in an amount averaging from 0.02 to 0.30 grams per day.

5. The method of claim 1, wherein said lipid-soluble thiamine is administered orally.

6. The method of claim 5, wherein the amount of lipid-soluble thiamine is administered in an amount averaging from 0.02 to 0.30 grams per day.

7. The method of claim 5, wherein said lipid soluble thiamine is administered orally in the form of capsules, tablets, caplets, food, or a beverage.

8. The method of claim 7, wherein the dose is administered via capsules or tablets containing lipid-soluble thiamine in addition to or in admixture with an inert, non-toxic pharmaceutical carrier.

9. A method for improvement of cognitive function or for treatment of cognitive dysfunction, said method comprising administering to a subject a therapeutically effective amount of a lipid-soluble thiamine or a prodrug thereof in an amount averaging from about 0.02 to about 0.5 grams per day per 70 kg body weight over a period of three months or longer.

10. The method of claim 9, wherein said lipid-soluble thiamine is selected from the group consisting of thiamine propyl disulfide, thiamine tetrahydrofurfuryl disulfide, thiamine allyl disulfide, thiamine (7-methoxycarbonyl-3-acetylthioheptyl)disulfide, thiamine 2-hydroxyethyl disulfide, and O-benzoylthiamine disulfide.

11. The method of claim 10, wherein the lipid-soluble thiamine is administered orally or parenterally.

12. The method of claim 9, wherein said lipid-soluble thiamine is administered in an amount of from about 0.05 to 0.30 grams per day for a 70 kg adult human.

13. The method of claim 12, wherein administration is orally in the form of capsules, tablets, caplets, food, or a beverage.

14. The method of claim 13, wherein the capsules, tablets or caplets contain lipid-soluble thiamine in addition to or in admixture with an inert, non-toxic pharmaceutical carrier.

15. A method for preventing Age-Associated Memory Impairment, said method comprising administering to a subject a therapeutically effective amount of a lipid-soluble thiamine or a prodrug thereof in an amount averaging from about 0.02 to about 0.5 grams per day per 70 kg body weight over a period of three months or longer.

16. The method of claim 15, wherein said lipid-soluble thiamine is selected from the group consisting of thiamine propyl disulfide, thiamine tetrahydrofurfuryl disulfide, thiamine allyl disulfide, thiamine (7-methoxycarbonyl-3-acetylthioheptyl)disulfide, thiamine 2-hydroxyethyl disulfide, and O-benzoylthiamine disulfide.

17. The method of claim 15, wherein said lipid soluble thiamine is administered orally in the form of capsules, food, or a beverage.

* * * * *